Figure 1:
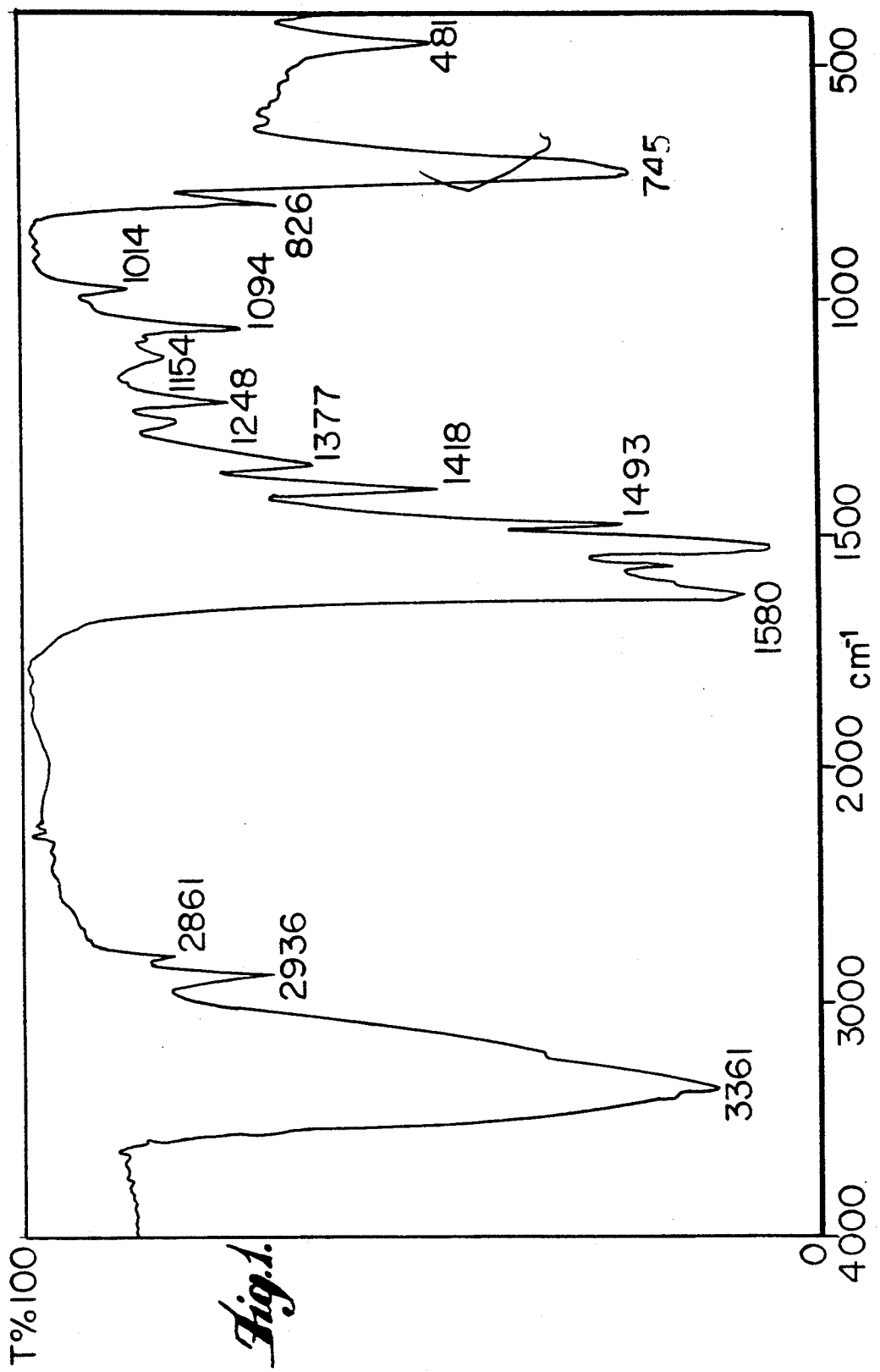

United States Patent [19]
Rheinberger et al.

[11] Patent Number: 5,304,369
[45] Date of Patent: Apr. 19, 1994

[54] CHLOROHEXIDINE ADDUCT AND METHOD OF PREPARING SAME

[75] Inventors: Volker Rheinberger, Vadnz, Liechtenstein; Ulrich Salz, Weissenberg, Fed. Rep. of Germany; Peter Burtscher, Nütziders, Austria

[73] Assignee: Ivoclar AG, Schaan, Liechtenstein

[21] Appl. No.: 965,019

[22] Filed: Oct. 23, 1992

[30] Foreign Application Priority Data

Oct. 26, 1991 [DE] Fed. Rep. of Germany ....... 4135397

[51] Int. Cl.$^5$ ..................... C07C 279/18; A61K 7/18; A61K 31/155
[52] U.S. Cl. ....................... 424/52; 424/49; 424/54; 514/635; 564/235
[58] Field of Search ............................ 424/49, 52, 54; 564/235; 514/635

[56] References Cited

FOREIGN PATENT DOCUMENTS 0211511 8/1956 Austria ................................ 564/235
2158150 5/1972 Fed. Rep. of Germany .

Primary Examiner—Richard L. Raymond
Assistant Examiner—Peter G. O'Sullivan
Attorney, Agent, or Firm—Cushman, Darby & Cushman

[57] ABSTRACT

A chlorohexidine adduct comprising one molecule of chlorohexidine with six molecules of hydrogen fluoride and a process for its preparation are described, said adduct displaying a high anti-bacterial effectiveness vis-à-vis *Streptococcus mutans* even in very small concentrations and being valuable as anti-plaque agent and for caries prevention.

4 Claims, 3 Drawing Sheets

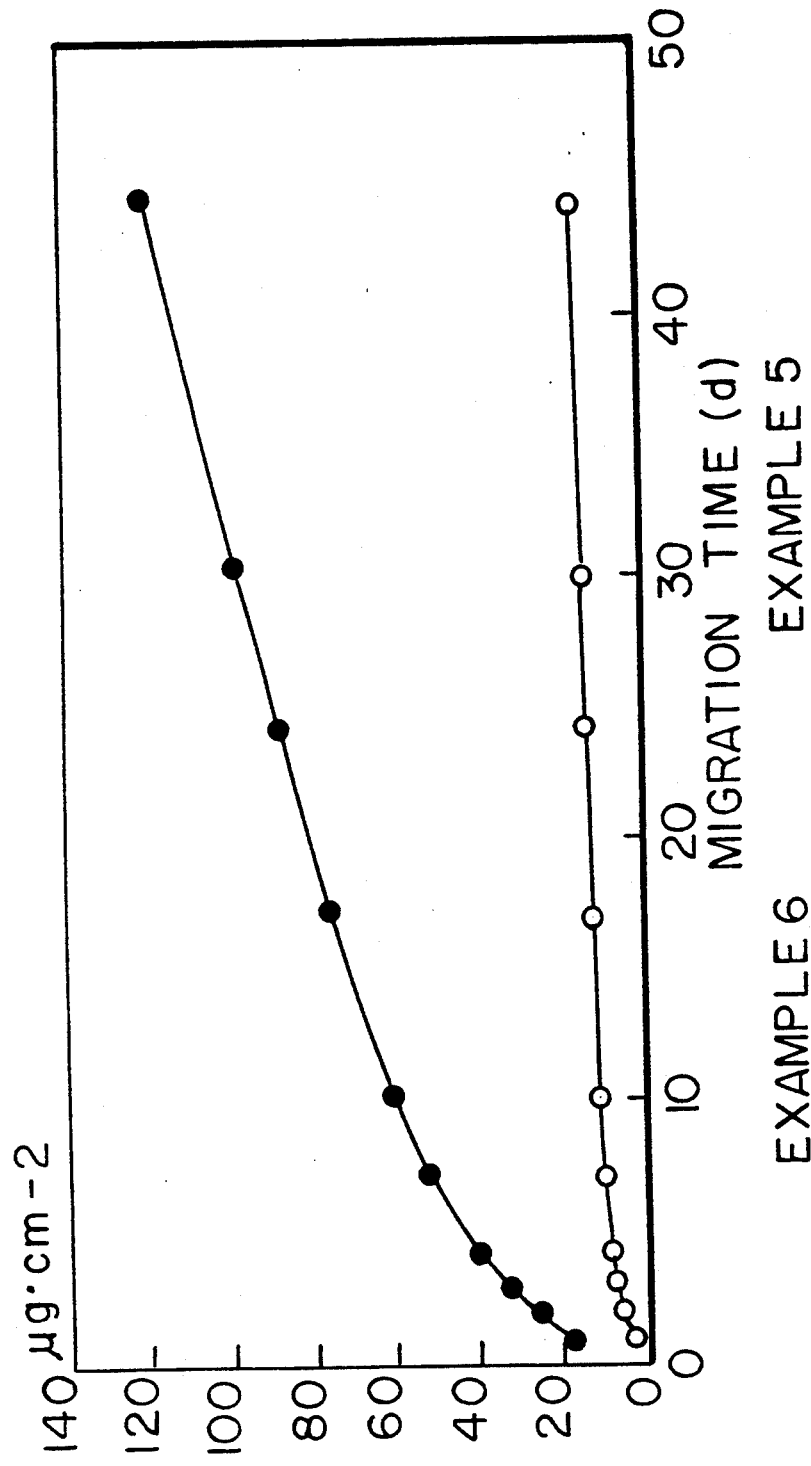

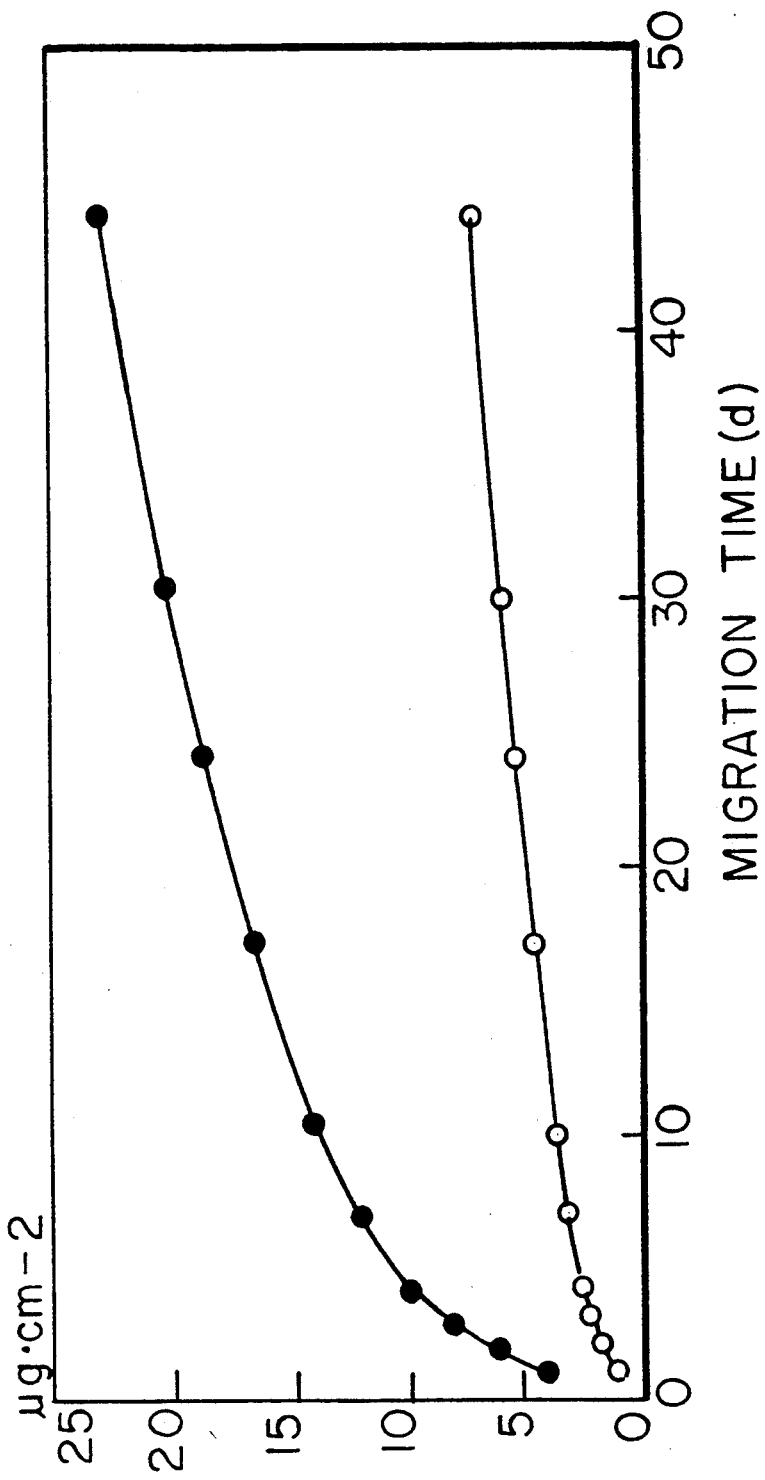

CHLOROHEXIDINE ADDUCT AND METHOD OF PREPARING SAME

The invention relates to a chlorohexidine adduct which can be used as an antiseptic and in particular as an antiseptic in dentistry and also as a therapeutic and prophylactic anti-plaque agent. In the attempt to inhibit or completely stop the formation of plaque and thus also of caries, the effectiveness of substances with antibacterial properties such as e.g. chlorinated phenols, formaldehyde and quaternary ammonium compounds has been examined in the past. However, they have not been used in practice, because of their toxicity and their restricted action spectrum The currently most effective anti-plaque agent is chlorohexidine (1,6-bis-($N^5$-p-chlorophenyl-$N'$-diguanido)-hexane), which is used in particular in the form of its water-soluble digluconate, but also as sparingly soluble diacetate and dihydrochloride (cf. A. Scheie in J. Dent. Res. 68, 1609 (1989) and P. Gjermo in J. Dent. Res. 68, 1602 (1989)). Known in addition to these chlorohexidine compounds is also chlorohexidine dihydrofluoride, which according to published German patent application 21 58 150 is used as an antiseptic agent in transparent tooth gels.

It has been shown that chlorohexidine as a chemotherapeutic product is effective against bacteria of the type *Streptococcus mutans*. Bacteria of this type play a key part in the formation of caries It is therefore assumed that, with a reduction of their quantity on the surface of the teeth, caries formation can be countered effectively (cf. I. Ostela and J. Tenovuo in Scand. J. Dent Res. 98, 1 (1990)).

The bactericidal effect exerted by chlorohexidine vis-à-vis bacteria of the type *Streptococcus mutans* is, however, greatly weakened if it is used in small concentrations Therefore, chlorohexidine is also subjected to clear restrictions in practical application if it is a matter of reducing tooth plaque which for its part can lead to the occurrence of parodontosis and caries. Moreover, the application of chlorohexidine in higher concentrations can lead to unwanted dis-colorations of the tongue, teeth, prostheses and fillings (cf. L. Flötra, P. Gjermo, G. Rölla and J. Waerhaug in Scand J. Dent. Res. 79, 119 (1971)).

It is therefore the object of the invention to make available a chlo-rohexidine adduct which is generally usable as an antiseptic and in particular can be used as an anti-plaque agent, said adduct effec-tively countering the renewal and growth of films on the teeth, even in very small concentrations, and moreover being able, by giving off fluoride, to protect the tooth enamel against demineralization, especially by acids.

This object is achieved by the novel chlorohexidine adduct and the process for its preparation as well as its use.

The chlorohexidine adduct according to the invention is a compound of the following formula:

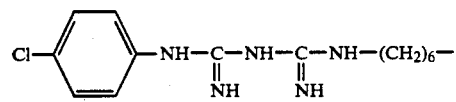

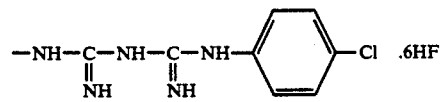

or its hydrates.

The adduct displays the IR spectrum according to FIG. 1. It is not known how the six molecules of hydrogen fluoride in the adduct according to the invention are bound to the chlorohexidine molecule. It is conceivable in principle that the adduct according to the invention consists of uncharged molecules or is present in the form of ions and thus as salt.

The adduct according to the invention is prepared by reacting a solution of hydrogen fluoride with a solution of chlorohexidine salt, the molar ratio of hydrogen fluoride to chlorohexidine salt being at least 6:1, and separating the resultant adduct. If a molar ratio of hydrogen fluoride to chlorohexidine salt of less than 6:1 is used, the adduct according to the invention is also obtained, but in a smaller yield.

The chlorohexidine adduct according to the invention is preferably prepared by reacting a solution of hydrogen fluoride in water with a solution of chlorohexidine salt in water in a molar ratio of hydrogen fluoride to chlorohexidine salt of 6:1 to 30:1 at a temperature in the range from ambient temperature to reflux temperature, and separating the resulting precipitate.

To achieve high yields and prepare a precipitate of the chlorohexidine adduct according to the invention which is easily separable by filtration, a molar ratio of hydrogen fluoride to chlorohexidine salt of 10:1 to 20:1 is especially preferred. Solutions in a mixture of ethanol/water 90/10 vol.-% are used to advantage at reflux temperature instead of the aqueous solutions of the adducts. In this case, only a molar ratio of hydrogen fluoride to chlorohexidine salt of 8:1 is necessary. The adduct according to the invention is produced in a high yield of more than 95% in this case. Because of the smaller hydrogen fluoride requirement, this variant of the preparation process is especially preferred.

Chlorohexidine digluconate is used preferably for the preparation of the adduct according to the invention. However, other chlorohexidine salts which are adequately soluble in the solvent used in each case, such as e.g. the dihydrochloride or the diacetate, can also be used.

24 hours are typically adequate as reaction duration in order to achieve a complete reaction. The reaction duration can vary, however, depending on the chosen reaction parameters. However, the reaction duration best suited in each case can easily be ascertained by routine experiments.

The chlorohexidine adduct which occurs predominantly as precipitate during the reaction is preferably separated and cleaned by filtration and subsequent washing with water and acetone. Further chlorohexidine adduct can be obtained by working up the mother liquors, so that overall yields of 91 to nearly 100% are achievable. The purified solid is then dried in a known manner and is present, depending on the degree of drying, in the form of hydrates with various water contents. The drying is preferably carried out at 50° C. in the drying chamber.

Because of its pronounced antibacterial action, the chlorohexidine adduct according to the invention can be used generally as an antiseptic agent. It can be used both in pharmaceutical and cosmetic products as a therapeutic and prophylactic bactericide. However, it is preferably used in dental materials, such as e.g. tooth varnishes, fissure sealants, prophylactic pastes, mouthwashes, toothpicks, dental floss, dental chewing gum, dressings, tooth ointments, gum trainers, disinfectants for prostheses and modelling materials, drying agents, underfilling materials, cements, filling materials, adhesion promoters and endodontosis materials. The adduct according to the invention can be deposited on a fixed substrate, such as e.g. a toothpick or dental floss, or incorporated into dental materials, such as e.g. provisional filling materials and fissure sealants.

Particularly advantageous is the incorporation of the adduct according to the invention into dental materials which are to remain in the oral cavity for a limited period, such as e.g. provisional filling materials, dressings, modelling materials and temporary cements. If the adduct according to the invention is incorporated for example into a provisional filling material, one obtains after its removal a germ-free cavity into which the final filling can be placed immediately.

As the chlorohexidine adduct displays only quite a low solubility in common solvents, it is preferably incorporated into the said dental materials as a solid. It is added to the dental materials in quan-tities of 0.1 to 20 wt.-%, preferably 1 to 10 wt.-%, and particularly preferably 3 to 7 wt.-%, relative to the total weight of the material. Examples of usable dental materials are those which contain 10 to 95 wt.-% of polymerizable organic binder, 5 to 90 wt.-% of inorganic and/or organic fillers and 0.01 to 5 wt.-% of catalysts, based on the total weight of the material.

Solutions containing 0.001 to 0.03 wt.-% of adduct according to the invention may also be used. Suitable as solvents are, for example, water, ethanol, acetone, ethyl acetate, triethylene glycol dimethacrylate and decandiol methacrylate. Synthetic or natural resins which are soluble in common solvents and become hard after the evaporation of the solvents can also be used. Examples of these are shellac, benzoin resin, polyvinyl pyrrolidone and rosin.

Another preferred application of the chlorohexidine adduct is that as a therapeutic or prophylactic anti-plaque agent. It prevents the renewal of films on teeth and inhibits the growth of already existing films on teeth. Diseases caused by the presence of films on teeth, such as e.g. parodontosis, primary and secondary caries and gingivitis, can thus be combatted effectively with the chlorohexidine adduct according to the invention.

With regard to its bactericidal effectiveness, the adduct according to the invention is completely comparable in a concentration of 0.03 wt.-% with the chlorohexidine currently rated as a very effective anti-plaque agent. Surprisingly, however, the effectiveness of chlorohexidine is clearly exceeded if both are used in concentrations smaller than or equal to 0.01 wt.-%. In this concentration range, the chlorohexidine adduct according to the invention is also clearly superior to stannous difluoride, a compound which is known for having very good bactericidal properties.

The superiority of the adduct according to the invention especially in small concentrations is of particular importance for practical application, as deposited active ingredients are continuously diluted as a result of the permanent saliva flow in the oral cavity. An active ingredient like the chlorohexidine adduct according to the invention, which also displays a marked bactericidal effect in small concentrations, is therefore of particular advantage.

Another advantage compared to chlorohexidine is that, when the adduct according to the invention is used, there are no unwanted side-effects such as a bitter taste, discolorations of tooth materials and irritations of the mucosa.

Finally, the high fluorine content of the adduct according to the invention means that the latter protects the tooth enamel through fluoridation and can therefore also afford effective protection against the formation of caries in this respect.

The invention is explained in more detail in the following examples.

Example 1

To prepare the chlorohexidine adduct according to the invention, 42.5 ml of an aqueous 20% (0.01 mole) chlorohexidine digluconate solution were added under stirring dropwise within 2 hours to 45 ml of an aqueous 4.4% (0.11 mole) HF solution. The mixture was stirred further overnight, and the precipitate which formed was filtered and washed threetimes with 50 ml of water each time and then twice with 50 ml of acetone each time. The resultant precipitate was then dried at 50° C. in the drying chamber. The chlorohexidine adduct according to the invention was obtained as a solid in a yield of 76% and had a melting point of 185° to 190° C.

The IR spectrum (KBr moulding) is reproduced in FIG. 1. Elementary analysis shows that the product is chlorohexidine hexahydrofluoride with one to two moles of crystal water.

| Structure A: | | |
|---|---|---|
| $C_{22}H_{30}N_{10}Cl_2 \cdot 6HF \cdot H_2O$ | | MW = 642.9 |
| Structure B: | | |
| $C_{22}H_{30}N_{10}Cl_2 \cdot 6HF \cdot 2H_2O$ | | MW = 660.9 |
| Elementary analysis: | | |
| | | theoretical |
| | found | Structure A | Structure B |
| C | 41.00% | 41.06% | 39.95% |
| H | 5.15% | 5.60% | 5.45% |
| N | 21.70% | 21.78% | 21.18% |
| Cl | 10.85% | 11.02% | 10.73% |
| F | 17.55% | 17.73% | 17.25% |
| $H_2O$*) | 3.75% | 2.80% | 5.45% |

*)$H_2O$ content determined by the Karl Fischer method

The solubility of the adduct according to the invention in some common solvents and reactive diluents is given in the following Table I:

TABLE I

| | |
|---|---|
| Water (pH value 2 to 9.7) | 0.03 wt. % |
| Ethanol | 0.005 wt. % |
| Acetone | 0.03 wt. % |
| Ethyl acetate | 0.02 wt. % |
| Triethylene glycol dimethacrylate (SR-205) | <0.005 wt. % |
| Decandiol dimethacrylate (D$_3$MA) | <0.005 wt. % |

EXAMPLE 2

By using 90 ml of an aqueous 4.4% (0.2 mole) HF solution and 42.5 ml of an aqueous 20% (0.01 mole) chlorohexidine digluconate solution - the reaction procedure otherwise being the same as in Example 1 —a precipitate was obtained which was more easily filterable than the one obtained according to Example 1.

The chlorohexidine adduct was obtained in a higher yield of 91 to 94%.

EXAMPLE 3

42.5 ml (0.01 mole) of an aqueous 20% chlorohexidine digluconate solution were added dropwise to 200 ml (0.08 mole) of a solution of hydrogen fluoride in a 90/10 vol.-% mixture of ethanol/water at reflux temperature for 1 hour, accompanied by stirring, and the stirring was continued for a further hour. After the reaction mixture had cooled to ambient temperature the resultant precipitate was filtered off and washed three-times, each time with 50 ml of a 90/10 vol.-% mixture of ethanol/water. In contrast to the preparation processes carried out at ambient temperature as in Example 1 and Example 2, the resultant precipitate was crystalline and thus easily filterable. Further product came out of the mother liquor within a further week. The total yield was 98%.

Compared to the process variants according to Examples 1 and 2, the advantage with this process procedure in a mixture of ethanol/water at reflux temperature is that a better filterable precipitate occurs in a very high yield and the hydrogen fluoride requirement is much smaller.

EXAMPLE 4

The antibacterial effectiveness of the chlorohexidine adduct according to the invention was demonstrated in the Agar diffusion test with *Streptococcus mutans*.

For this purpose, culture suspensions of *Streptococcus mutans* were added to a liquid Agar comprising yeast extract and dextrose. After the Agar plates had solidified, a hole of 10 mm diameter was cut out, into which 0.1 ml of the solution to be tested was poured in each case. After 24 hours of incubation at 37° C., the diameters of the inhibiting zones were measured for each sample, which were duplicated in each case. The results of these tests are reproduced in the following Table II.

TABLE II

| Concentration | Inhibiting zone diameters | | |
|---|---|---|---|
| | Solution A | Solution B | Solution C |
| 0.03 wt. % | 17 mm | 17 mm | 20 mm |
| 0.01 wt. % | 13 mm | 15 mm | 11 mm |
| 0.003 wt. % | 11 mm | 12 mm | 10 mm* |

*Not effective

It transpires that in the concentration range of 0.03 wt.-% the antibacterial effectiveness of the chlorohexidine adduct according to the invention vis-à-vis *Streptococcus mutans* is comparable with that of chlorohexidine gluconate, while stannous difluoride displays an even stronger action in this concentration range. However, increasing dilution is accompanied by markedly declining effectiveness in the case of the known compounds, to such an extent indeed in the case of stannous difluoride at a concentration of 0.003 wt.-% that an antibacterial action can no longer be detected. Compared to this, the antibacterial effectiveness of the adduct according to the invention is still very high even at concentrations of 0.01 to 0.003 wt.-%. Its superiority especially in low concentrations thus makes it a very effective anti-plaque agent.

EXAMPLE 5

A light-curable fissure sealant contains the following constituents:

| | |
|---|---|
| 56.08 wt. % | bisphenol A glycidyl methacrylate (Bis-GMA) |
| 36.1 wt. % | triethylene glycol dimethacrylate |
| 0.45 wt. % | cyanoethylmethylaniline |
| 0.25 wt. % | DL-camphor quinone |
| 2.1 wt. % | $TiO_2$ |
| 0.02 wt. % | 2,6-di-tert.-butyl-p-cresol |
| 5.0 wt. % | chlorohexidine adduct |

The light-curable fissure sealant was obtained by mixing all the components. The sealant was applied with a brush onto the fissures in a molar tooth and hardened for 20 sec with the Heliolux ® light-curable apparatus made by Vivadent/Liechtenstein. In this way the fissures were permanently sealed and, because of the fluoride liberated by the chlorohexidine adduct incorporated into the sealant, excellent protection against caries was achieved in the occlusal area.

As a result of the admixture of 1 to 5 wt.-% of the chlorohexidine adduct to the basic fissure-sealant formulation, no decrease in through-hardening depth was observed, as the following values for Vickers hardness show:

| | HV 0.5 |
|---|---|
| Fissure sealant without chlorohexidine adduct | 188 MPa |
| Fissure sealant + 1% chlorohexidine adduct | 248 MPa |
| Fissure sealant + 3% chlorohexidine adduct | 212 MPa |
| Fissure sealant + 5% chlorohexidine adduct | 180 MPa |

To detect chlorohexidine and fluoride migration, 10 test specimens, each 50 mm in diameter and 0.5 mm high, were stored in dist. water at 37° C. The fluoride ion concentration was determined by means of a fluoroelectrode and the chlorohexidine concentration was ascertained by means of UV spectroscopy. The cumulative figure for liberated fluoride and chlorohexidine is summarized in Table III.

TABLE III

| Migration time [days] | Fluoride liberated [µg/cm$^2$] | Chlorohexidine liberated [µg/cm$^2$] |
|---|---|---|
| 1 | 0.95 | 3.86 |
| 2 | 1.48 | 5.56 |
| 3 | 1.91 | 6.84 |
| 4 | 2.22 | 7.58 |
| 7 | 2.91 | 9.26 |
| 10 | 3.45 | 10.30 |
| 17 | 4.22 | 11.60 |
| 24 | 4.92 | 12.30 |
| 30 | 5.58 | 13.20 |
| 44 | 6.56 | 14.40 |

The results are represented graphically in FIGS. 2 and 3.

EXAMPLE 6

A light-curable dental material with relatively high water absorption and thus high active ingredient release (e.g. suitable as provisional filling material or as a dressing) has the following composition:

| | |
|---|---|
| 43.6 wt. % | polyester urethane dimethacrylate |
| 0.25 wt. % | cyanoethylmethylaniline |
| 0.15 wt. % | DL-camphor quinone |

-continued

| | | |
|---|---|---|
| 35.0 wt. % | splinter polymerizate | |
| 21.0 wt. % | amorphous SiO₂, silanized (BET surface 50 m²/g) | |

The splinter polymerizate comprises:

| | | |
|---|---|---|
| 59.4 wt. % | urethane dimethacrylate | |
| 40 wt. % | fine-particled SiO₂, silanized | |
| 0.6 wt. % | benzpinacol. | |

The components are mixed together and polymerized at 120° C. The filled polymerizate is ground into a polymer powder.

The amorphous fine-particled silanized SiO₂ is Aerosil ® OX 50 from Degussa AG.

A light-curable dental material was obtained by mixing all the components.

The water absorption of dental filling composites is normally in the range of 1 wt.-%; this material displays a water absorption in the range of 3 wt.-% (3 weeks H₂O storage at 37° C.). The cumulative amount of fluoride and chlorohexidine liberated is summarized in Table IV.

TABLE IV

| Migration time [days] | Fluoride given off [μg/cm²] | Chlorohexidine given off [μg/cm²] |
|---|---|---|
| 1 | 3.78 | 17.0 |
| 2 | 6.03 | 25.7 |
| 3 | 8.03 | 33.6 |
| 4 | 9.82 | 40.3 |
| 7 | 11.98 | 51.4 |
| 10 | 13.99 | 60.6 |
| 17 | 16.37 | 74.5 |
| 24 | 18.68 | 86.6 |
| 30 | 19.88 | 97.8 |
| 44 | 22.68 | 118.3 |

The results are represented graphically in FIGS. 2 and 3.

As the migration tests show, significant quantities of fluoride and chlorohexidine are released from this dental material, so that an adequate inhibition of the growth of microorganisms is also to be expected in this combination.

Since not all microorganisms react identically to released active ingredients, studies were conducted using the following microbes.

| | |
|---|---|
| Gram-positive bacteria: | *Streptococcus mutans* |
| | *Staphylococcus aureus* |
| Gram-negative bacteria: | *Pseudomonas auruginosa* |
| | *Escherichia coli* |
| Fungus: | *Candida albicans* |

Test specimens (d=10 mm, h=2 mm) were inserted into the moist microorganism cultures at 37° C. over a period of 24 hours and the inhibiting zone was then determined.

| | Inhibiting zone diameter [mm] |
|---|---|
| *Streptococcus mutans* | 15 |
| *Staphylococcus aureus* | 16 |
| *Pseudomonas auruginosa* | 17 |
| *Escherichia coli* | 15 |
| *Candida albicans* | 12 |

A clear inhibition of growth can be established for these different microorganisms.

We claim:

1. Chlorohexidine adduct having the following formula

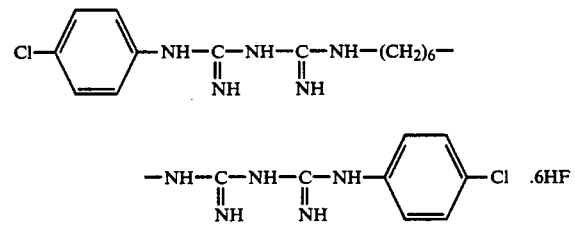

and its hydrates

2. An antiseptic and anti-plaque composition comprising the chlorohexidine adduct or its hydrates according to claim 1.

3. A method of preventing the formation of bacteria in the mouth or destroying bacteria already present in the mouth comprising applying said chlorohexidine adduct of claim 1 or its hydrates to a dental material and applying said dental material to the mouth.

4. A method of preventing dental caries comprising applying said chlorohexidine of claim 1 or its hydrates to a dental material and applying said dental material to the mouth.

* * * * *